(12) United States Patent
Takahashi (10) Patent No.: US 6,473,116 B1
(45) Date of Patent: Oct. 29, 2002

(54) ELECTRONIC ENDOSCOPE

(75) Inventor: Tadashi Takahashi, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/471,368

(22) Filed: Dec. 23, 1999

(30) Foreign Application Priority Data

Dec. 28, 1998 (JP) .......................................... 10-373721

(51) Int. Cl.⁷ ................................................. H04N 7/18
(52) U.S. Cl. ...................................................... 348/65
(58) Field of Search .............................. 348/65, 68–72, 348/625; 600/101, 109, 112, 180, 181; H01N 7/18

(56) References Cited

U.S. PATENT DOCUMENTS

| | | | |
|---|---|---|---|
| 4,322,129 A | | 3/1982 | Takahashi et al. |
| 4,561,429 A | * | 12/1985 | Sato et al. ..................... 348/69 |
| 4,885,634 A | * | 12/1989 | Yabe ........................... 348/71 |
| 4,898,175 A | * | 2/1990 | Noguchi ..................... 600/109 |
| 5,159,380 A | | 10/1992 | Furuya et al. |
| 5,184,159 A | | 2/1993 | Furuya et al. |
| 5,184,170 A | | 2/1993 | Takahashi et al. |
| 5,191,369 A | | 3/1993 | Furuya et al. |
| 5,237,403 A | | 8/1993 | Sugimoto et al. |
| 5,239,378 A | * | 8/1993 | Tsuji et al. ................. 348/625 |
| 5,269,289 A | * | 12/1993 | Takehana et al. ........... 600/109 |
| 5,272,497 A | | 12/1993 | Furuya et al. |
| 5,277,172 A | | 1/1994 | Sugimoto |
| 5,347,994 A | | 9/1994 | Takahashi et al. |
| 5,475,420 A | * | 12/1995 | Buchin ........................ 348/65 |
| 5,488,509 A | | 1/1996 | Takahashi et al. |
| 5,608,451 A | * | 3/1997 | Konno et al. ................. 348/69 |
| 6,319,198 B1 | * | 11/2001 | Takahashi ................... 600/181 |

* cited by examiner

Primary Examiner—Richard Lee
(74) Attorney, Agent, or Firm—Greenblum & Bernstein, P.L.C.

(57) ABSTRACT

Electronic endoscope includes a video-scope, video-processor, a light source, a luminance value calculator, a stop, a motor, a drive-amount setter, a stop-controller, and a drive-amount determiner. The luminance value calculator successively calculates a luminance value indicating brightness of the object image, on the basis of image-pixel signals. The drive-amount setter sets a target drive-amount of the stop, to make the brightness of the object image constant, on the basis of the luminance value. The stop-controller adjusts the quantity of light radiating from the distal end of the video-scope by controlling the stop in accordance with the target drive-amount at regular time-intervals, whereby the stop opens and closes such that the brightness of the object image at constant level. The drive-amount determiner determines whether the target drive-amount exceeds a tolerable drive-amount. When the target drive-amount exceeds a tolerable drive-amount, the stop-controller at least suspends a drive of the stop at the next adjustment of the quantity of light.

16 Claims, 7 Drawing Sheets

| |Y0−vr| | PULSE NUMBER |
|---|---|
| 0 − 7 | 1 |
| 8 − 15 | 2 |
| 16 − 31 | 4 |
| 32 − 47 | 8 |
| 48 − 63 | 16 |
| 64 − 95 | 24 |
| 96 − 127 | 36 |
| 128 − 255 | 48 |

ELECTRONIC ENDOSCOPE

BACKGROUND OF THE INVENTION

1. Field of the Invention

This invention relates to an electronic endoscope for displaying a body-cavity image on a TV monitor, the endoscope having a video-scope with an image sensor and a video-processor. In particular, the present invention relates to adjusting the brightness of an object image.

2. Description of the Related Art

In an electronic endoscope, a video-scope includes an optical light guide extended therethrough, which is formed as a bundle of optical fibers. A video-processor includes a light source, such as a halogen lamp. When the video-scope is connected to the video-processor, a proximal end of the optical light guide is optically connected to the light source. Thus, an object to be photographed is illuminated by light radiating from a distal end of the optical light guide, and an object image is formed on the image sensor provided at the distal end of the video-scope. Then, the object image, formed on the image sensor, is converted into analog image-pixel signals by photoelectric conversion.

The analog image-pixel signals are fed to the video-processor and are suitably processed, so that video signals are generated. The video signals are then output to a TV monitor, thus a body-cavity image (for example, a stomach image) is displayed on the monitor.

In general, to maintain proper brightness of the object image displayed on the monitor, a quantity of light radiating from the distal end of the optical light guide should be automatically regulated. In a conventional endoscope, for regulation of the quantity of light, a stop (diaphragm) provided between the light source and the proximal end of the light guide is controlled, such that the brightness of the object image displayed on the monitor is maintained at a constant level. The luminance value, indicating the brightness of the object image, is successively calculated on the basis of the image-pixel signals, and then the control of the stop is performed at regular time-intervals. In controlling the stop, the drive-amount of the stop is determined on the basis of the difference between the luminance value and a reference value. Note, the luminance value is, for example, an average value of one frame worth, and the reference value is, for example, a middle value of a range of luminance values (from 0 to 255), which corresponds to the proper brightness of the object image.

However, in the conventional automatic adjustment of the quantity of light, a drive time of the stop becomes very long when the determined drive-amount of the stop is large. The luminance value is successively calculated independently of the drive-amount of the stop. Therefore, the stop is occasionally driven on the basis of the preceding luminance value.

When the stop is driven in error, the brightness of the object image formed on the image sensor having already been corrected, hunting, in which the stop does not converge to a proper position for a long time, occurs, so that the brightness of the object image can not be quickly adjusted properly.

On the other hand, if the regulation of the quantity of light is performed at longer time-intervals in order to solve the above problems, the stop cannot be rapidly controlled when the brightness of the object image changes considerably.

SUMMARY OF THE INVENTION

Therefore, an object of the present invention is to provide an electronic endoscope that can properly adjust brightness of an object image by controlling the stop, without causing hunting.

An electronic endoscope of the present invention includes a video-scope, video-processor, a light source, a luminance value calculator, a stop, a motor, a drive-amount setter, a stop-controller, and a drive-amount determiner. The video-scope has an image sensor, provided at a distal end of the video-scope, on which an object image is formed, and a light guide provided throughout the video-scope, to guide light from a proximal end of the video-scope to the distal end of the video-scope. The video-processor, to which the proximal end of the video-scope and a monitor for displaying the object image are respectively connected, processes image-pixel signals corresponding to the object image, successively read from the image sensor. The light source is provided in the video-processor such that light, emitted from the light source, is guided through the light guide and radiates from the distal end of the video-scope. The luminance value calculator successively calculates a luminance value indicating brightness of the object image, on the basis of the image-pixel signals. The stop is provided between the light source and the proximal end of the video-scope, and regulates a quantity of light radiating from the distal end of the video-scope. The motor drives the stop, the stop being connected to the motor such that the stop is driven in accordance with a motion of the motor. The drive-amount setter sets a target drive-amount of the stop, to make the brightness of the object image constant, on the basis of the luminance value. The stop-controller adjusts the quantity of light radiating from the distal end of the video-scope by controlling the stop in accordance with the target drive-amount at regular time-intervals, whereby the stop opens and closes such that the brightness of the object image displayed on the monitor is maintained at constant level. Then, the drive-amount determiner determines whether the target drive-amount exceeds a tolerable drive-amount. When the target drive-amount exceeds a tolerable drive-amount, the stop-controller at least suspends driving of the stop at the next adjustment of the quantity of light.

BRIEF DESCRIPTION OF THE DRAWINGS

The present invention will be better understood from the description of the preferred embodiment of the invention set forth below together with the accompanying drawings, in which.

DESCRIPTION OF THE PREFERRED EMBODIMENT

Hereinafter, the preferred embodiment of the present invention is described with reference to the attached drawings.

Figure 1:
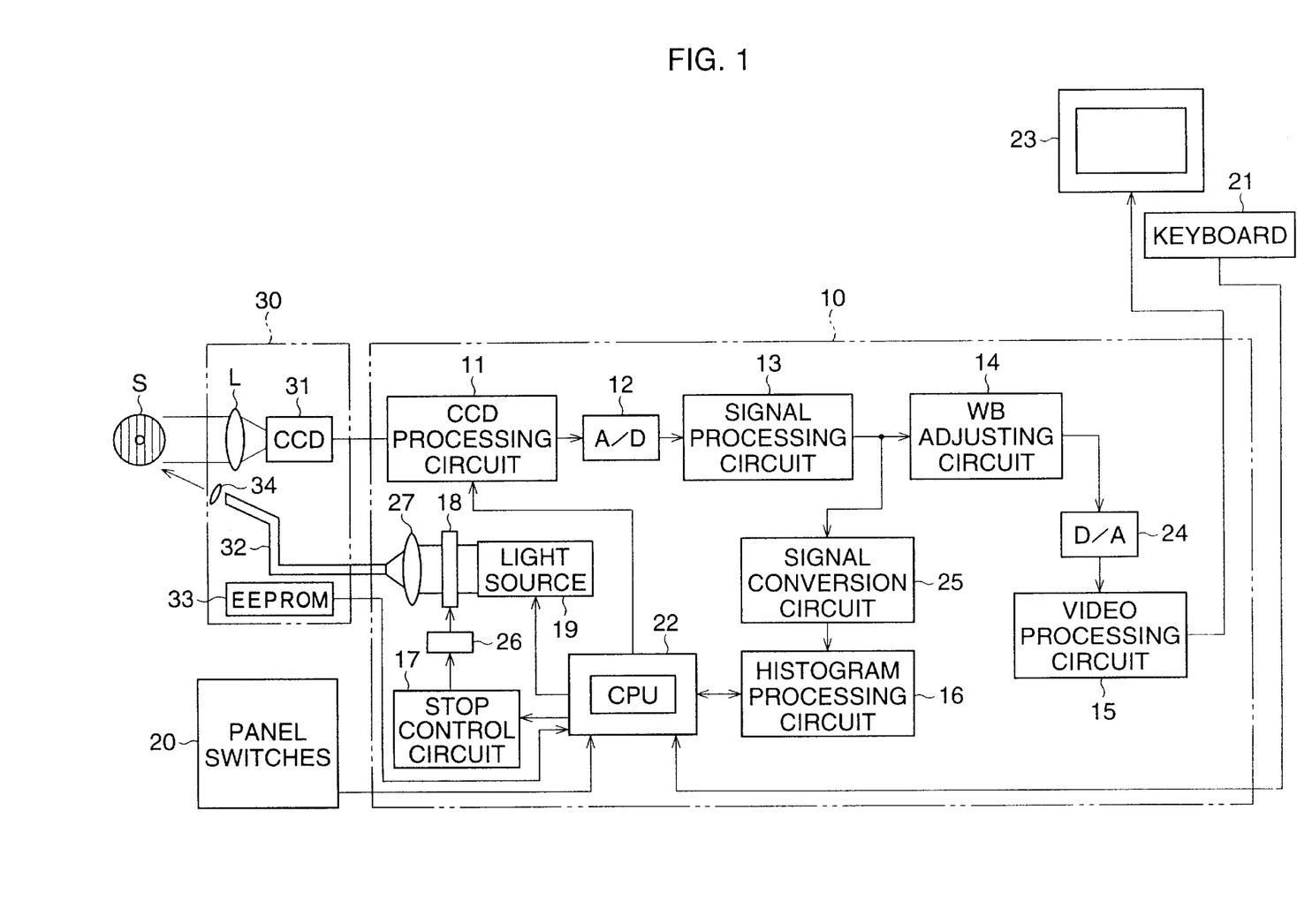
FIG. 1 is a block diagram of the embodiment of the present invention.

FIG. 1 is a block diagram of an electronic endoscope of the embodiment. This endoscope is used when an operation, an inspection or a treatment of an organ, such as a stomach, is performed.

The electronic endoscope includes a video-processor 10 and a video-scope 30. The video-scope 30 is a flexible conduit, and is detachably connected to the video-processor 10. Further, a monitor 23 for displaying an image is also connected to the video-processor 23. During an operation or the like, a proximal end of the video-scope 30 is connected to the video-processor 10, and the video-scope 30 is inserted into the body-cavity to display the body-cavity image on the monitor 23.

The video-scope 30 includes a light guide 32 extended therethrough, formed as a bundle of optical fibers. When the proximal end of the video-scope 30 is connected to the video-processor 10, the proximal end of the light guide 32 is optically connected to a light source 19, such as a halogen lamp, provided in the video-processor 10. Thus, light, emitted from the light source 19, is directed to the proximal end of the light guide 32 via a condenser lens 27, and then radiates from the distal end of the light guide 32 toward an object S via a diffusion lens 34.

A stop (diaphragm) 18 is provided between the light source 19 and the proximal end of the light guide 32, and is driven by a stepping motor 26, which rotates in accordance with pulse signals output from a CPU (Central Processing Unit) 22. The stop 18 is provided for regulating a quantity of light directed from the light source 19 to the proximal end of the light guide 32. Namely, the stop 18 is provided for adjusting a quantity of the illuminating-light radiating from the distal end of the video-scope 30, such that brightness of the object image displayed on the monitor 23 is maintained at constant level. In a EEPROM (Electronically Erasable Programmable ROM) 33, data associated with a type of the video-scope 30 etc., is stored, and read by the CPU 22 when the video-scope 30 is connected to the video-processor 10.

A CCD (Charge-Coupled-Device) 31, which is an image sensor, is provided at the distal end of the video-scope 30. When the object S is illuminated by the illuminating-light, light reflected from the object S is focused on the CCD 31 via an optical lens L, so that the object image is formed on the CCD 31.

Photoelectric conversion devices (not shown) are provided on the CCD 31, and red (R), green (G), and blue (B) color mosaic-filter elements are provided in front of the photoelectric conversion devices. The object image, formed on the CCD 31, is converted into electrical image-pixel signals corresponding to predetermined colors by the photoelectric conversion devices. These analog image-pixel signals, corresponding to one frame worth, are then successively read from the CCD 31 to a CCD processing circuit 11. Namely, the object image is scanned. In this embodiment, NTSC method is applied as a color-television video-standard. Although other video-standard may be used in alternative embodiments. In the NTSC method, the one frame worth of analog image-pixel signals is scanned at regular time-intervals of 1/30 sec.

In the CCD processing circuit 11, one frame worth of the analog image-pixel signals, output from the CCD 31 in order, is separated into analog image-pixel signals corresponding to the red R, analog image-pixel signals corresponding to green G, analog image-pixel signals corresponding to blue B. Then, the analog image-pixel signals, corresponding to each color (R, G, B), are amplified and fed to an A/D converter 12, and are converted into digital image-pixel signals, respectively. The digital image-pixel signals, corresponding to each color, are fed to a signal processing circuit 13.

In the signal processing circuit 13, the digital image-pixel signals are subjected to various image-processes, such as a reset noise reduction and gamma-correction and etc., and are then output to both a signal conversion circuit 25 and a white-balance adjusting circuit 14.

In the signal conversion circuit 25, luminance signals of one frame worth are successively generated on the basis of the digital image-pixel signals, and fed to a histogram processing circuit 16. In the histogram processing circuit 16, the luminance signals are input, and then subjected to a histogram processing, so that histogram-data are generated. The histogram-data are read from the histogram processing circuit 16 by the CPU 22. Note that the electronic endoscope as a whole is controlled by the CPU 22.

In the CPU 22, an average luminance value, as described later, is calculated on the basis of the histogram-data, and then the average luminance value is compared with a reference value stored in a memory (not shown). On the basis of a difference between the reference value and the average luminance value, control-signals, in short, pulse signals are fed from the CPU 22 to the stop control circuit 17, and then driver-signals are fed to the stepping motor 26, so that the stop 18 is driven. Thus, the quantity of the illuminating-light radiating from the distal end of the light guide 32 is regulated. Note, in the stop control circuit 17, a logic sequencer and an exciting-circuit (both not shown) are provided. Based on the pulse signals input to the logic sequencer, an exciting current is fed from the exciting-circuit to the stepping motor 26, thus the stepping motor 26 rotates.

In the white balance circuit 14, the digital image-pixel signals are subjected to a white balance adjustment processing. In this embodiment, the digital image-pixel signals are adjusted such that the ratio of R, G, B signals is respectively "1:1:1" when a white object is photographed by the video-scope 30. After the white balance adjustment processing is performed, the digital image-pixel signals are fed to a D/A converter 24.

In the D/A converter 24, the digital image-pixel signals are converted into analog image-pixel signals, and then fed to a video processing circuit 15. In the video processing circuit 15, the analog image-pixel signals are converted into the video signals, such as NTSC signals, and then output to the monitor 23. Then, one frame worth of the video signals are successively output to the monitor 23 at regular time-intervals of 1/30 sec, thus, the object image is displayed on the monitor 23, as a moving picture.

When panel switches 20 are operated by an operator to set a level of a brightness of the light source 19 and so on, a operation-signal is input to the CPU 22, thus the brightness of the light source 19 is set. Similarly, when a keyboard 21 is operated, the operation-signal is input to the CPU 22. Thus, for example, a picture on the monitor 23 is changed.

Figure 2:
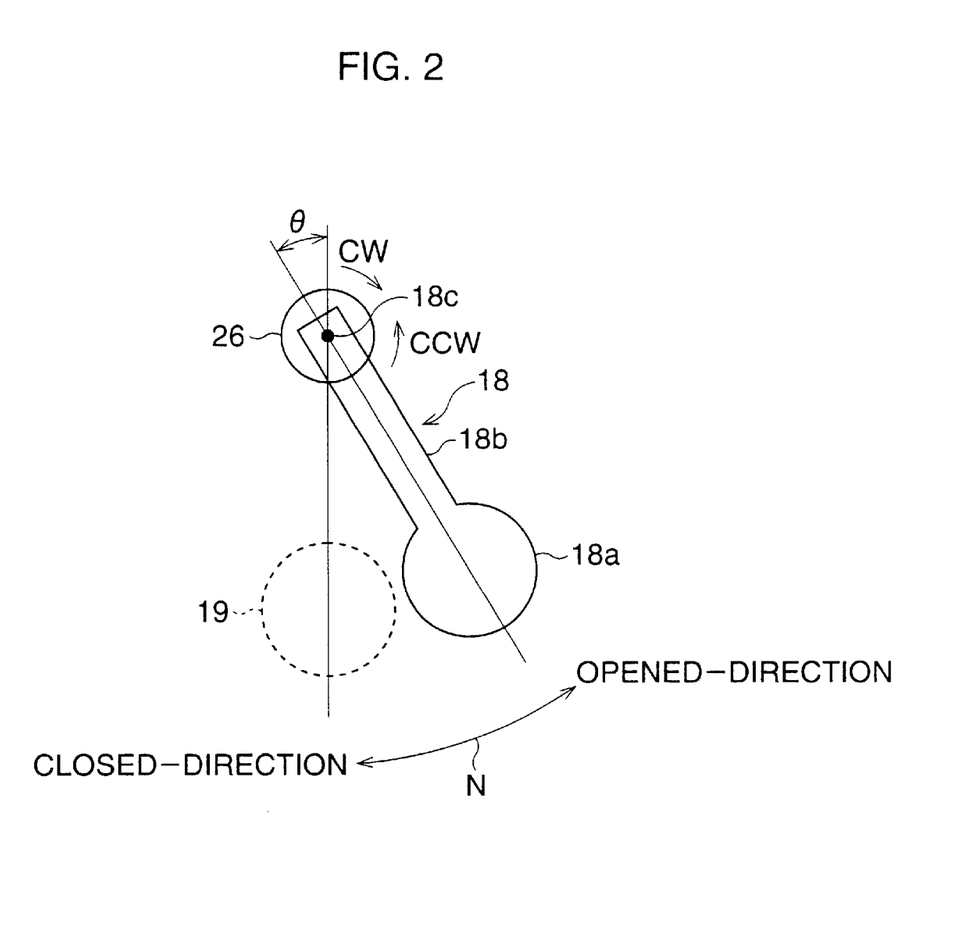
FIG. 2 is a plan view showing a stop and a stepping motor.

FIG. 2 is a front view showing the stop 18 and the stepping motor 26 (shown in FIG. 1).

The stop 18 comprises a cover member 18a having a disk-like configuration, and a support arm 18b having an elongated plate configuration, extended from the cover member 18a.

The support arm 18b of the stop 18 is rotatably connected to the stepping motor 26 via a gear (not shown). When the stepping motor 26 rotates, the stop 18 pivots on a pivot 18c in accordance with a rotation of the stepping motor 26. At this time, a motion of the stop 18 draws an arc, as shown in an arc arrow N, such that the cover member 18a covers light radiating from the light source 19. Herein, a direction in which the cover member 18a approaches the light source 19 is defined as a closed-direction, and conversely, a direction in which the cover member 18a retreats from the light source 19 is defined as an opened-direction. Note, light, emitted from the light source 19, is a parallel pencil of rays, and further a magnitude of the cross-section of the parallel pencil of rays is not beyond a magnitude of the diameter of a surface of the cover member 18a. Therefore, the cover member 18 can cover light radiating from the light source 19.

In the stop control circuit 17 (shown in FIG. 1), a direction signal is fed from the CPU 22 with the pulse signals. When the direction signals is a H (High) level, the stepping motor 26 rotes clockwise (CW). Thus, the stop 18 pivots in the closed-direction. Specifically, the stop 18 closes down. Conversely, when the direction signal is a L (low) level, the stepping motor 26 rotates counterclockwise (CCW). Thus, the stop 18 pivots in the opened-direction. Namely, the stop 18 opens. Therefore, the quantity of light passing through the stop 18, namely, the quantity of light radiating from the distal end of the light guide 32, changes in accordance with a position of the cover member 18a.

A rotation angle e of the stop 18, shown in FIG. 2, indicates an opening-degree of the stop 18. The rotation angle θ is defined as approximately θ when the cover member 18a completely blocks light radiating from the light source 19. Therefore, the rotation angle e increases as the stop 18 pivots toward the opened-direction. Conversely, the rotation angle θ decreases as the stop 18 pivots toward the closed-direction. When the stop 18 is fully open, the rotation angle θ is approximately 30°. Namely, the stop 18 is pivotable between approximately 0° to 30°. When the rotation angle θ is approximately 30°, substantially all of the light radiating from the light source 19 passes through the stop 18.

On the other hand, a rotation position of the stepping motor 26 is represented by a rotation-position variable p. A relationship between the rotation angle θ and the rotation-position variable P is shown as follows:

$$\theta = p/8 \tag{1}$$

Namely, the rotation angle "1°" corresponds to the rotation-position variable p of "8". Therefore, when the stop 18 is fully open (θ=30°), the rotation-position variable p is "240". When the rotation-position variable p is changed from 240 to 120, the rotation-angle θ is changed from 30° to 15°.

In this way, the relationship between the rotation-angle θ and the rotation-position variable p is a linear relationship. Further, the opening-degree of the stop 18 is indicated by the rotation-position variable p. For example, when the rotation-position variable p is 120, the opening-degree of the stop 18 is half of that when the stop 18 is fully open, as the rotation angle "15°" is half of the rotation angle "30°".

The stepping motor 26 rotates depending upon a pulse number of the pulse signals, which are fed from the CPU 22. Namely, a drive-amount of the stop 18 (herein, the rotation angle θ) depends on the pulse number. In this embodiment, the rotation-position variable p changes by "1" when one pulse is fed to the stop control circuit 17. Therefore, a shifting angle (Δθ) of "1°" of the stop 18 corresponds to the pulse number "8". For example, when the pulse signals of pulse number "16" and the direction signal of the L level are fed to the stop control circuit 17, in a case where the rotation-position variable p is 120 (the rotation angle θ=15°), the stepping motor 26 rotates counterclockwise such that the rotation-position variable p is changed from 120 to 136. At this time, the stop 18, the rotation angle θ of which is "15°", pivots in the opened-direction by "2°", so that the rotation angle θ becomes "17°".

In this way, the quantity of light passing through said stop 18, in short, the quantity of light radiating from the distal end of said light guide 32, is adjusted by controlling the stop 18.

Figure 3:
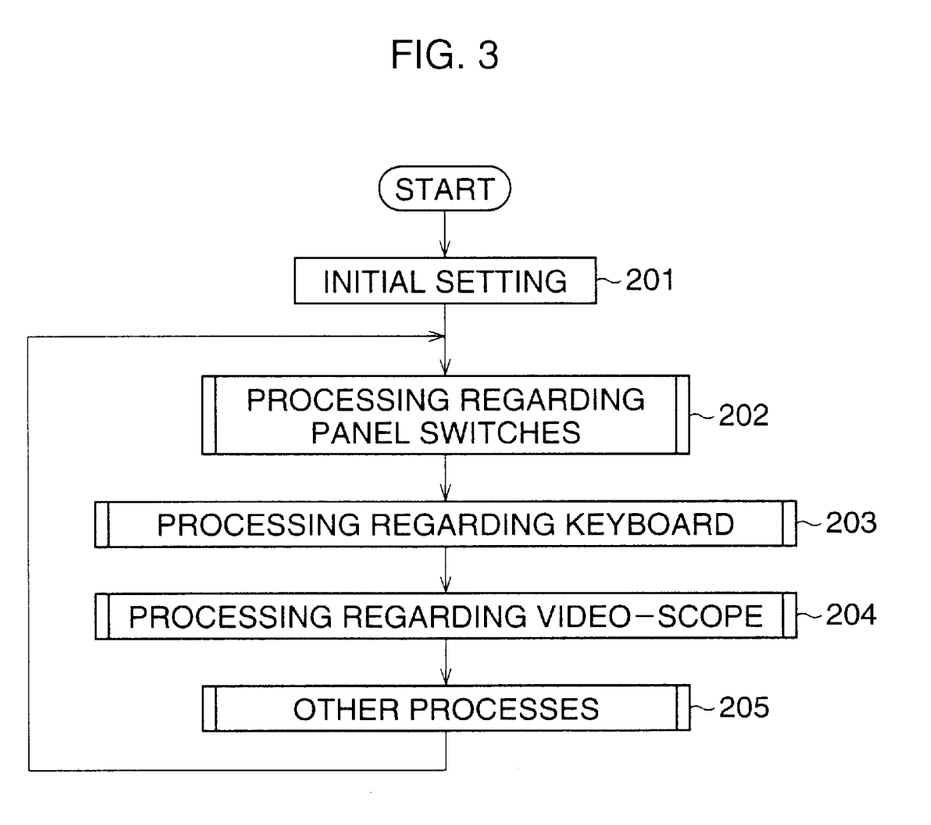
FIG. 3 is a view showing a main routine.

FIG. 3 is a flowchart showing a main routine regarding operations of the electronic endoscope as a whole. When electric power is turned ON, the main routine is started.

In Step 201, the stop 18, the light source 19 etc., are set to an initial setting, respectively. For example, the stop 18 is set to an initial position.

In Step 202, processing regarding the manipulation of the panel switches is performed. For example, a level of the brightness of the light source 19 is determined in accordance with the operation of the panel switches 20. In Step 203, processing regarding the manipulation of the keyboard 21 is performed. For example, the picture on the monitor 23 is changed in accordance with the manipulation of the keyboard 21. In Step 204, processing regarding the video-scope 30 is performed. For example, a scope-name of the video-scope 30 is displayed on the monitor 23 when the video-scope 30 is newly connected to the video-processor 10. In Step 205, other processes are performed. For example, real-time may be displayed on the monitor 23.

These operations of the electronic endoscope are executed until the electric power is turned OFF. In each Step, a subroutine is respectively performed. When the panel switches 20 are not operated at Step 202, the process goes to Step 203. Similarly, when the keyboard 21 is not operated at Step 203, Step 203 is not executed, and the process goes to next Step 204.

Figure 4:
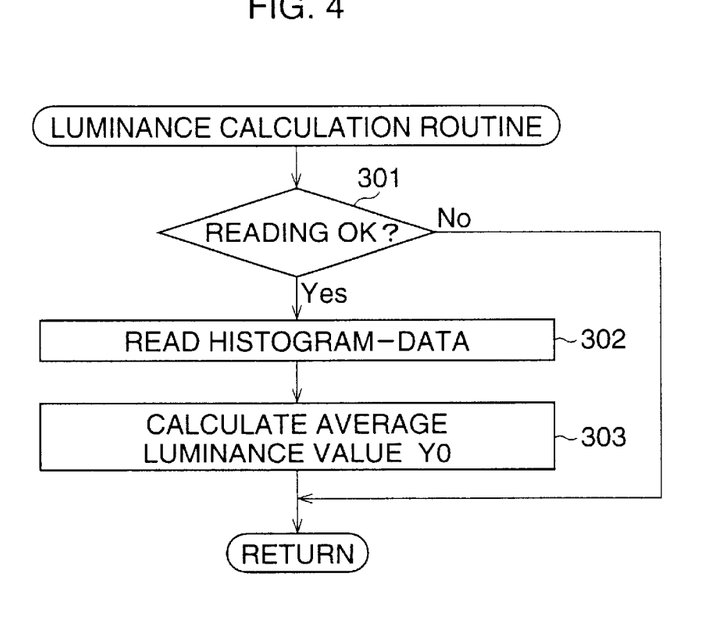
FIG. 4 is a view showing an interrupt routine associated with a calculation of an average luminance value.

FIG. 4 is view showing an interrupt routine regarding calculating the average luminance value Y0. This interrupt routine interrupts the operations of the electronic endoscope shown in FIG. 3, and is performed at time-intervals of 4/1000 sec. Herein, the interrupt routine is represented by "luminance-calculation routine"

In Step 301, it is determined whether or not reading of the histogram-data from the histogram processing circuit 16 is possible. When it is impossible to read the histogram data from the histogram processing circuit 16, the processing of Step 302 and 303 is not executed. On the other hand, when it is possible to read the histogram-data from the histogram processing circuit 16, the process goes to Step 302. Note that, when the histogram-data corresponding to one frame worth of the luminance signals are not generated or the luminance signals have not been written in the histogram processing circuit 16, it is impossible to read the histogram-data.

In Step 302, the histogram-data corresponding to one frame worth of the object image are read and then fed to the CPU 22.

Figure 5:
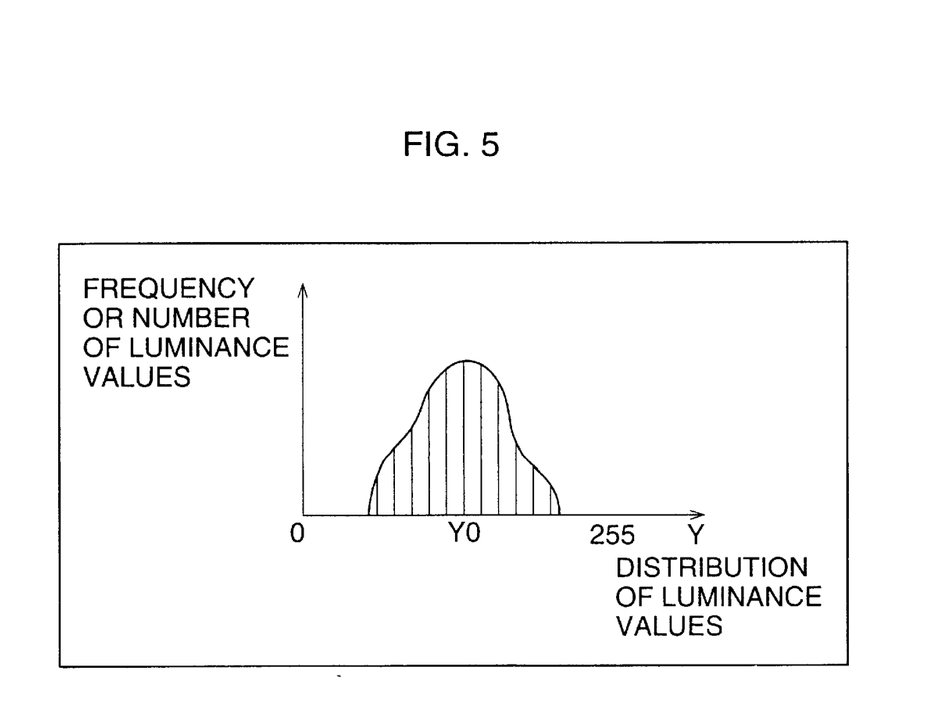
FIG. 5 is a view showing histogram-data.

FIG. 5 is a view showing the histogram-data. In the histogram-data, a horizontal direction represents a distribution of luminance values Y included in one frame, and a vertical direction represents a frequency or number of the luminance values Y. Note, in one frame worth of the luminance signals, the range of each luminance value Y, corresponding to each pixel on the CCD 31, is from 0 to 255.

In Step 303 shown in FIG. 4, the average luminance value Y0 is calculated on the basis of the histogram-data. The average luminance value Y0 is an average value of one frame worth of luminance values Y, and indicates brightness of the object image displayed on the monitor 23. Note, the calculation of the average luminance value on the basis of the histogram-data is conventionally well known.

After the average luminance value Y0 is calculated, the luminance-calculation routine is terminated.

Figure 6:
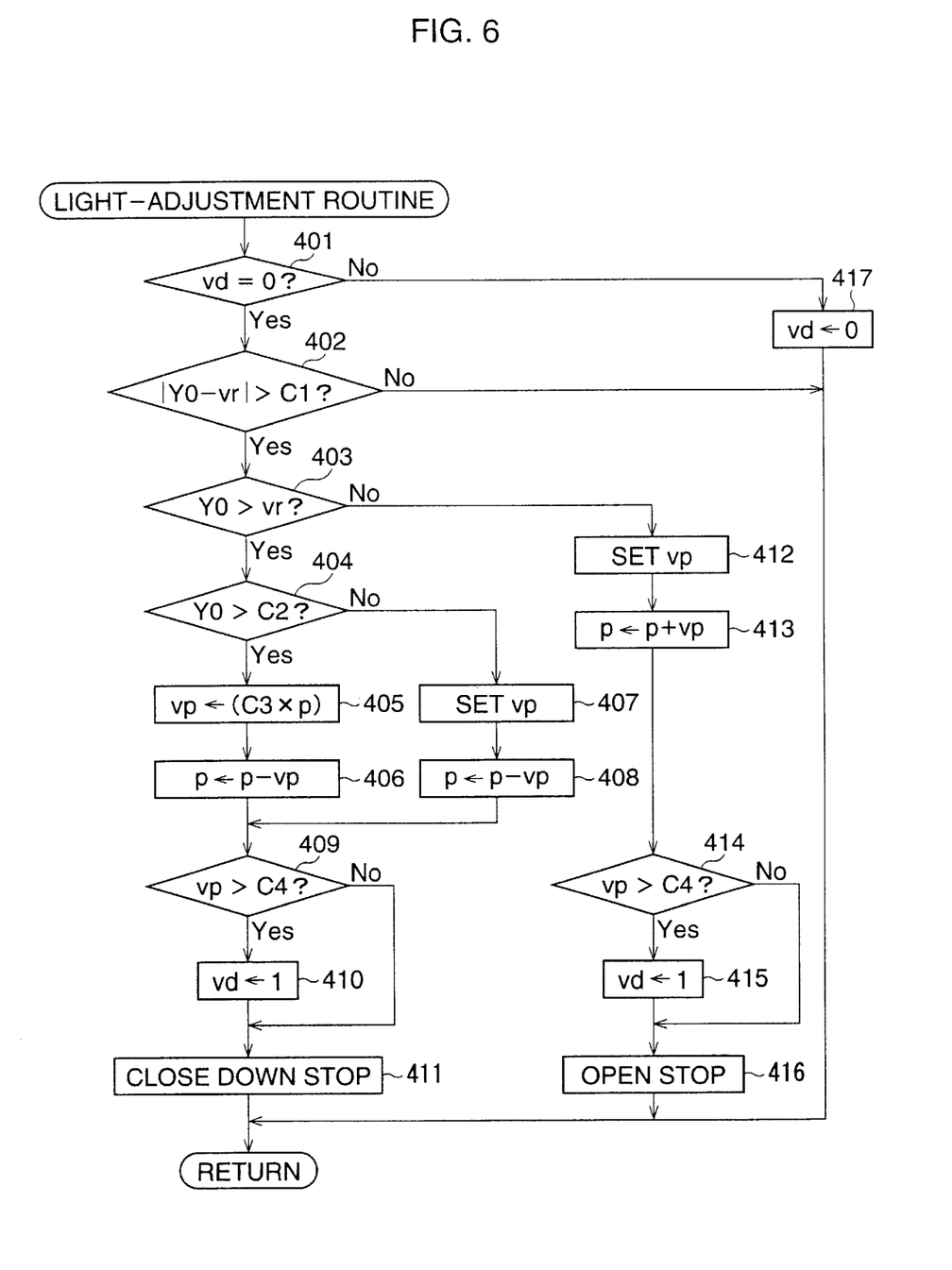
FIG. 6 is a view showing an interrupt routine associated with an adjustment of a quantity of light.

FIG. 6 is a view showing an interrupt routine regarding the adjustment of light radiating from the distal end of video-scope 30. This interrupt processing interrupts the operations of the electronic endoscope shown in FIG. 3, and is performed at time-intervals of 1/30 sec to correspond to a period of scanning one frame of the object image formed on the CCD 31, namely, NTSC method. Herein, this interrupt routine is represented by "light-adjustment routine".

In Step 401, it is determined whether or not an execution variable vd is "0". The execution variable vd is a variable for determining whether the adjustment of the quantity of light is performed, and a value of the execution variable vd is one of "0" and "1". The execution variable "0" indicates that the adjustment of the quantity of light by the stop 18 is performed in the present interrupt routine. On the other hand, the execution variable "1" indicates that the adjustment of the quantity of light by the stop 18 is not performed in the present interrupt routine.

When it is determined that the execution variable vd is "0", the process goes to Step 402. On the other hand, when it is determined that the execution variable vd is "1", the interrupt routine is terminated. Namely, the adjustment of the quantity of light is not substantially performed.

In step 402, it is determined whether or not a difference between the average luminance value Y0 and a reference value vr "$|Y0-vr|$" is more than an allowance-value C1. The reference value vr is an average luminance value in a case where the brightness of the object image formed on the CCD 31 is proper. In this embodiment, the reference value vr is predetermined to "128". Namely, the reference value vr is predetermined to a middle value of the range of the luminance values Y (from 0 to 255). In this connection, the reference value vr can be changed by operating the panel switches 20 (shown in FIG. 1). The allowance-value C1 represents a permissible margin of error. In this embodiment, the allowance-value C1 is predetermined to "4".

When it is determined that the difference $|Y0-vr|$ is not more than the allowance-value C1 (=4) at Step 402, the interrupt routine is terminated. Namely, the adjustment of the quantity of light is not performed, as the average luminance value Y0 is substantially equal to the reference value vr. On the other hand, when it is determined that the difference $|Y0-vr|$ is more than the allowance-value C1 (=4), the process goes to Step 403.

In Step 403, it is determined whether or not the average luminance value Y0 is more than the reference value vr. When it is determined that the average luminance value Y0 is more than the reference value vr, the process goes to Step 404. In Steps 404 to 411, processing for closing down the stop 18 is performed.

In Step 404, it is determined whether the average luminance value Y0 is more than a halation luminance value C2, namely, whether halation occurs on the object image displayed on the monitor 23. The halation luminance value C2 is an average luminance value in a case where the brightness of the object image results in halation. Namely, when the average luminance value Y0 exceeds the halation luminance value C2, a halation occurs on the object image displayed on the monitor 23. Generally, when the average luminance value Y0 exceeds about "200", halation occurs on the object image. In this embodiment, the halation luminance value C2 is predetermined to 220.

On the other hand, when it is determined that the average luminance value Y0 is not more than the halation luminance value C2 at Step 404, the process goes to Step 407. In Step 407, the pulse number vp is set on the basis of a reference table T shown in FIG. 7.

Figure 7:
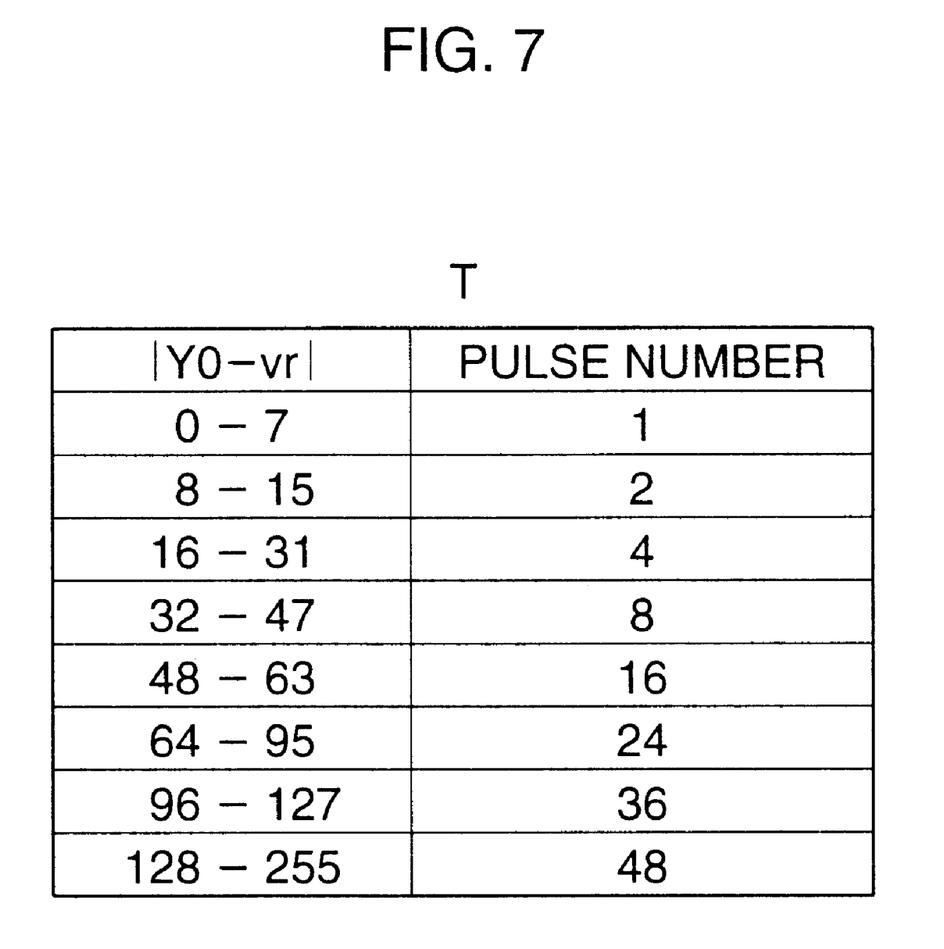
FIG. 7 is a view showing a reference table.

As shown in FIG. 7, the reference table T represents a correspondence relationship between the difference $|Y0-vr|$ and the pulse number vp. The pulse number vp set at Step 407 is a target pulse number, which corresponds to the drive-amount of the stop 18 necessary for maintaining the constant brightness of the object image. Therefore, the average luminance value Y0 approaches the reference value vr by driving the stop 18 by the pulse number vp. Herein, the drive-amount of the stop 18 corresponding to the determined pulse number vp is denoted by a target drive-amount. The pulse number vp depends upon a magnitude of the difference $|Y0-vr|$, namely, the pulse number vp increases as the difference $|Y0-vr|$ increases. In this embodiment, as shown in FIG. 7, a maximum pulse number corresponding to the difference between the average luminance value Y0 and the reference value vr "128–255" is determined to "48". In this way, the maximum pulse number vp shown in the reference table T is set to a relatively small value, so as not to cause hunting. A drive amount of the stop 18 corresponding to the maximum pulse number "48" is determined as 20% of the total drive amount of the stop 18 corresponding to the pulse number "240". Note, the reference table T is stored in a memory (not shown) provided in the CPU 30, shown in FIG. 1.

After the pulse number vp is determined at Step 407, the process goes to Step 408. In Step 408, the rotation-position variable p is determined on the basis of the pulse number vp as follows:

$$p \leftarrow p - vp \tag{2}$$

As described above, one pulse corresponds to the rotation-position variable "1". Therefore, for example, when the rotation-position variable p is "216" (the rotation angle $\theta=27°$) and the pulse number vp determined at Step 407 is "24", the rotation-position variable p is determined to "192" (the rotation angle $\theta=24°$). After Step 408 is performed, the process goes to Step 409.

On the other hand, when it is determined that the average luminance value Y0 is more than the halation luminance value C2 at Step 404, namely, that a halation occurs on the object image displayed on the monitor 23, the process goes to Step 405. In Step 405, the pulse number vp is determined without using the reference table T as follows:

$$vp \leftarrow C3 \times p (0.3 \leq C3 \leq 0.5) \tag{3}$$

Note that, a light-reduction coefficient is denoted by "C3". The light-reduction coefficient C3 is associated with the opening-degree of the stop 18, as described later. Then, the pulse number vp set at Step 405 is a reduction pulse number, which is determined when a halation occurs.

For example, when the light-reduction coefficient C3 is "0.4" and the current rotation-position variable p is 220 (the rotation angle $\theta=27.67°$), the pulse number vp is:

$$vp=0.4 \times 220=88 \tag{4}$$

Then, at Step 406, the rotation-position variable p is determined as follows:

$$p \leftarrow p - vp = p - C3 \times p = p(1-C3) \tag{5}$$

For example, when the pulse number vp determined at Step 405 is "88" and the current rotation-position variable p is "220", the rotation-position variable p is:

$$p \leftarrow 220-88=220(1-0.4)=132 \tag{6}$$

The rotation-position variable "132" corresponds to the rotation angle "16.5°". Therefore, the stop pivots in the closed-direction from angle "27.67°" to angle "16.5°". After the rotation-position variable p is determined, the process goes to Step 409.

At Step 409, it is determined whether the pulse number vp, determined at Step 405 or Step 407, exceeds a tolerable pulse number C4 as follows:

$$vp > C4 \tag{7}$$

Specifically, at step 409, it is determined whether the drive-amount of the stop 18 driven at the present interrupt routine is more than a tolerable drive-amount. Note that, the tolerable drive-amount is under a maximum drive-amount of a series of drive-amounts by which the hunting-situation does not occur. In this embodiment, the tolerable pulse number C4 is determined to "32". As described above, pulse number vp corresponds to the shifting angle $\Delta\theta$ of the stop 18. Accordingly, at Step 409, it is determined whether the stop 18 is pivoted more than 4° in the present interrupt routine, in short, whether the shifting angle $\Delta\theta$ exceeds "4°".

When it is determined that the pulse numbers vp exceeds the tolerable pulse number C4 at Step 409, the process goes to Step 410, wherein the execution variable vd is set to "1". Namely, at the next interrupt routine, the stop 18 is not driven. After the execution variable vd is set to "1", the process goes to Step 411.

On the other hand, when it is determined that the pulse number vp does not exceed the tolerable pulse number C4 at Step 409, the process skips Step 410 and goes directly to Step 411.

In Step 411, the pulse signals are fed to the stop control circuit 17. Thus, the stepping motor 26 rotates by the pulse number vp set at Step 405 or Step 407, depending upon the direction signal of the H level, and then the stop 18 is closed down. The stepping motor 26 rotates clockwise such that the rotation-position variable p becomes the rotation-position variable p determined at Step 406 or Step 408, and then the stop 18 pivots by the drive-amount corresponding to the pulse number vp. For example, the pulse number vp set at Step 407 is "24" in a case where the rotation-position variable p is "216" (the rotation angle $\theta=27°$), the stop 18 pivots in the closed-direction such that the rotation angle $\theta$ is changed from "27°" to "24°". After the pulse signals are fed to the stop control circuit 17 at Step 411, this interrupt routine is terminated.

When it is determined that the average luminance value Y0 is not more than the reference value vr at Step 403, the process goes to Step 412. In Steps 412 to 416, a processing for opening the stop 18 is performed.

In Step 412, the pulse number vp is determined on the basis of the reference table T shown in FIG. 7, similarly to Step 407. Then, at Step 413, the rotation-position variable p is determined in accordance with the pulse number vp determined at Step 412.

As the stop 18 is to be driven counterclockwise, the rotation-position variable p is determined as follows:

$$p \leftarrow p + vp \tag{8}$$

After the rotation-position variable p is determined, the process goes to Step 414. The execution of Step 414 and 415 is equal to the execution of Steps 409 and 410. After Steps 414 and 415 are performed, the process goes to Step 416.

In Step 416, the pulse signals are fed to the stop control circuit 17. Thus, the stepping motor 26 rotates counterclockwise by the pulse number vp determined at Step 412, depending upon the direction signal of the L level, and then the stop 18 is opened. Namely, the stepping motor 26 rotates such that the rotation-position variable p becomes the rotation-position variable p determined at Step 413, and then the stop 18 pivots by a drive-amount corresponding to the pulse number vp. After the pulse signals are fed to the stop control circuit 17 at Step 416, the interrupt routine is terminated. When the execution variable vd is set to "1" at Step 410 or Step 415, the control of the stop 18 is suspended at the next interrupt routine. At the next interrupt routine, the execution variable vd is set to "0" at Step 417, thus the stop 18 is driven at the next interrupt routine. Namely, the number of times of suspension of the control of the stop 18 is one time.

As described above, the relationship between the rotation-position variable p and the rotation angle $\theta$ is the linear relationship. When the relationship between the rotation-position variable p and the rotation angle $\theta$ is a nonlinear relationship, the determination of the pulse number vp at Step 405 is performed as follows.

Figure 8:
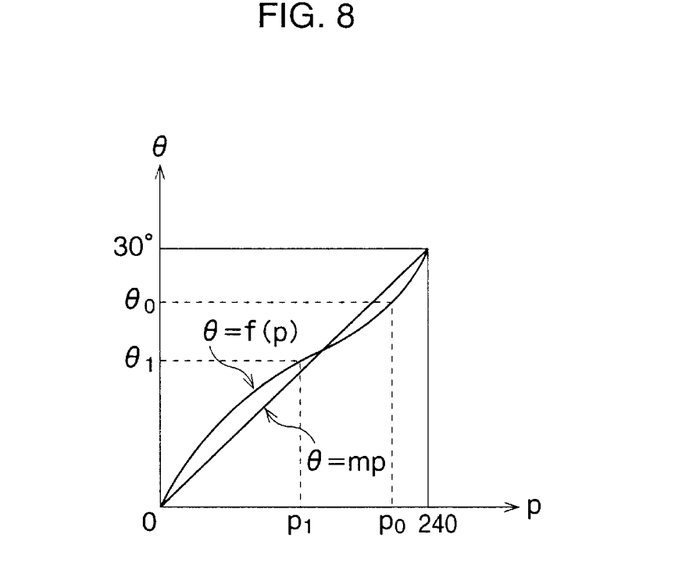
FIG. 8 is a view showing a relationship between a rotation-position variable of the stepping motor and a rotation angle of the stop.

FIG. 8 is a view showing the relationship between the rotational angle $\theta$ and the rotation-position variable p.

When the linear relationship between the rotational angle and the rotation-position variable p is maintained, the following equation is satisfied:

$$\theta = m \times p \, (m: \text{constant}) \tag{9}$$

In this embodiment, the constant m is "1/8". On the other hand, when the relationship between the rotational angle $\theta$ and the rotation-position variable p is the nonlinear relationship, the rotation angle $\theta$ is represented by:

$$\theta = f(p) \tag{10}$$

Note that, a function of the rotation-position variable p is denoted by "f".

The opening-degree of the stop 18 corresponds to the rotation angle $\theta$, as mentioned above. When equation (9) is satisfied, a ratio of an opening-degree corresponding to the rotation angle $\theta_1$ and an opening-degree corresponding to the rotation angle $\theta_0$ is represented as follows:

$$\theta_1/\theta_0 = m \times p_1/m \times p_0 = p_1/p_0 \tag{11}$$

Note that, the rotation-position variable $p_1$ corresponds to the rotation angle $\theta_1$, and the rotation-position variable $p_0$ corresponds to the rotation angle $\theta_0$.

When the pulse number vp is determined such that the stepping motor 26 rotates from the rotation-position variable $p_0$ to the rotation-position variable $P_1$, referring to equation (5), the equation (11) becomes:

$$\theta_1/\theta_0 = P_1/p_0 = p_0 \times (1-C3)/p_0 = 1-C3 \tag{12}$$

The opening-degree of the stop 18 corresponding to the rotation angle $\theta_1$ is "(1−C3)×100" percent of the opening-degree of the stop 18 corresponding to the rotation angle $\theta_0$. For example, when the light-reduction coefficient C3 is "0.4", the proportion of the opening-degrees of the stop 18 corresponding to the rotation angle $\theta_1$ to the opening-degrees of the stop 18 corresponding to the rotation angle $\theta_0$ is "0.6:1", as shown in the following equation:

$$\theta_1/\theta_0 = 1-C3 = 1-0.4 = 0.6 \tag{13}$$

The range of the light-reduction coefficient C3 is from 0.3 to 0.5, as described above. Therefore, at Step 405 in FIG. 6, the pulse number vp is determined such that the opening-degree of the stop 18 becomes one between 50% to 70% of the current opening-degree of the stop 18.

On the other hand, when equation (10) is satisfied, the pulse number vp is determined as follows.

As the relationship between the rotational angle θ and the rotation-position variable p is a one-to-one correspondence relationship, the rotation-position variable p is obtained by:

$$p = f^{-1}(\theta) \tag{14}$$

Note that, an inverse function of the function f is denoted by "$f^{-1}$"

As described above, one pulse number corresponds to the rotation-position variable p of "1". Therefore, when the rotation-position variable $p_0$ is changed to the rotation-position variable $p_1$, the pulse number vp for rotating the stepping motor 26 is:

$$vp = p_0 - p_1 = f^{-1}(\theta_0) - f^{-1}(\theta_1) \tag{15}$$

Referring to equation (12), the pulse number VP is obtained by:

$$vp = f^{-1}(\theta_0) - f^{-1}((1-C3) \times \theta_0) \tag{16}$$

Therefore, the equation (16) is utilized at Step 405 in a case where the relationship between the rotational angle θ and the rotation-position variable p is the nonlinear relationship.

In this embodiment, a swing-type stop 18 shown in FIG.2 is provided in the video-processor 10. In a modification, other types of stops, such as a blade-type stop and a U-shaped stop and the like, may be provided in the video-processor 10. Accordingly, if controlling the stop 18 on the basis of the quantity of light radiating from the distal end of the video-scope 30, the pulse number vp can be determined independently of the type of the stop 18 as follows.

Figure 9:
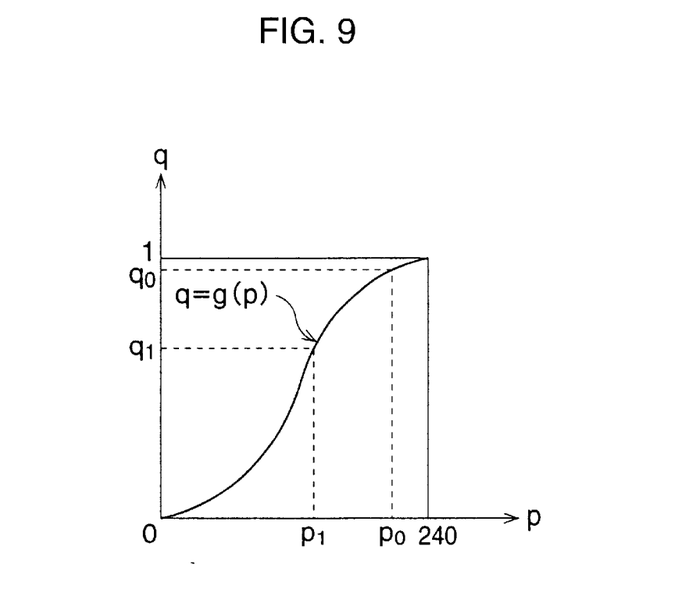
FIG. 9 is a view showing a relationship between the quantity of light and the rotation-position variable.

FIG. 9 is a view showing a relationship between the rotation-position variable p and the quantity of light q. Generally, the relationship between the rotation-position variable p and the quantity of light q is a nonlinear relationship. The quantity of light q indicates the quantity of light passing through the stop 18, i.e., the quantity of light radiating from the distal end of the light guide 32.

The relationship between the rotation-position variable p and the quantity of light q is represented as follows:

$$q = g(p) \tag{17}$$

Note that, a function of the quantity of light q is denoted by "g". Herein, the quantity of light q in a case where the stop is fully open is defined as "1".

Similarly to the opening-degree of the stop 18, when the quantity of light $q_1$ is "(1-C3)×100" percent of the quantity of light $q_0$, a ratio of the quantity of light $q_1$ to the quantity of light $q_0$ is:

$$q_1/q_0 = (1-C3) \tag{18}$$

Therefore, the pulse number vp is obtained by:

$$vp = p_0 - p_1 = g^{-1}(q_0) - g^{-1}(q_1) = g^{-1}(q_0) - g^{-1}((1-C3) \times q_0) \tag{19}$$

Note that, herein, an inverse function of the function g is denoted by "$g^{-1}$".

In this way, when the stop is to be driven such that the quantity of light q becomes "C3×100" percent of the current quantity of light q, the pulse number vp is determined by equation (19).

When the pulse number vp is large, a drive-time of the stop 18 is longer compared with the interrupt routine time, namely, scanning-time "1/30 sec" when the pulse number vp is large. When an adjustment of the quantity of light, which suspends the control of the stop 18 more than one interrupt routine, is performed, the execution variable vd is determined as follows.

The number of times, which the control of the stop 18 is suspended, is determined at Step 410 or Step 415 in accordance with the pulse number vp set at on θ of Step 405, Step 407 and Step 412. Then, a timing, which sets the execution variable vd to "0", is adjusted at Step 417. For example, a counter variable (from 0 to 3) corresponding to the suspending-times is set at Step 410 or Step 415, and then the counter variable set to one between "1" to "3" is counted, namely, decremented by 1 at Step 417. When the counter variable is 0, the execution variable is set to 0 at Step 417.

As described above, in this embodiment, when halation occurs on the object image displayed on the monitor 23, the pulse number vp is set at Step 405, such that the opening-degree of the stop becomes "(1-C3)×100" percent of the current opening-degree of the stop 18, independent of the reference table T. Then, at Step 411, the stepping motor 26 rotates clockwise by the pulse number vp, and the stop 18 closes down by the pulse number vp. Thus, the quantity of light radiating from the distal end of the video-scope 30 is reduced by a percentage corresponding to the light-reduction coefficient C3.

Considering that the rotation-position variable p in a case where halation occurs on the object image is usually more than "200", the pulse number vp set at Step 405 is more than the maximum pulse number "48" shown in the reference table T. Namely, the stop 18 frequently pivots in the closed-direction when halation occurs, as compared with when the stop 18 pivots on the basis of the maximum pulse number vp, shown in the reference table T. Therefore, the brightness of the object image soon becomes a proper brightness even if halation occurs on the object image.

Further, the drive-amount of the stop 18 at Step 411 depends upon the current opening-degree of the stop 18 (the rotation-position variable p), as shown in the equation (3). Therefore, even when halation occurs in a case where the opening-degree of the stop 18 is small (for example, the rotation angle θ=10°), an adjustment, in which the brightness of the object image displayed on the monitor 23 becomes too dark because of an over-drive of the stop 18, does not occur.

In this embodiment, the adjustment of the quantity of light is performed by controlling the stop 18. In a modification, the adjustment of the quantity of light may be performed by directly increasing and decreasing the quantity of light radiating from the light source 19, in place of the control of the stop 18. In this case, a voltage, which is supplied to the light source 19 is adjusted by the CPU 22. Further, the adjustment of the quantity of light may be performed by both the control of the stop 18 and the control of the light source 19.

Note, the range of the light-reduction coefficient "0.3≦C3≦0.5" may be set to "0.2≦C3≦0.8" in accordance with the type of the video-scope 30 used and the type of the light source 19 used.

As described above, in this embodiment, when the pulse number vp, set in one of Step 405, Step 407 and Step 412, exceeds the tolerable pulse number C4 (=32), namely, the drive-amount of the stop 18 exceeds a drive-amount corresponding to the shifting-angle "4°", the stop 18 is at least not driven at the next interrupt routine.

While the control of the stop 18 is suspended, the average luminance value Y0 is newly calculated at Step 303 in FIG.5. Then, when the suspension of the control of the stop 18 is terminated, the average luminance value Y0 corresponding to the present brightness of the object image is compared with the reference value vr at Step 403. Accordingly, even when the pulse number vp is set in a large number, namely, the drive-amount of the stop 18 becomes large, the stop 18 is driven on the basis of the present average luminance value Y0, so that hunting does not occur. Thus, the adjustment of the quantity of light is performed rapidly.

In this embodiment, the average luminance value Y0 is utilized in the adjustment of the quantity of light. In a modification, other luminance values, for example, the peak value of one frame worth of the luminance values Y, may be used on the adjustment of the quantity of light. Further, the average luminance value Y0 may be directly calculated on the basis of the luminance signals, without the histogram processing.

Finally, it will be understood by those skilled in the art that the foregoing description is of preferred embodiments of the device, and that various changes and modifications may be made to the present invention without departing from the spirit and scope thereof.

The present disclosure relates to subject matters contained in Japanese patent application no. 10-373721 (filed on Dec. 28, 1998) which is expressly incorporated herein, by reference, in its entirety.

What is claimed is:

1. An electronic endoscope comprising:

a video-scope that has an image sensor provided at a distal end of said video-scope, on which an object image is formed, and a light guide provided throughout said video-scope, to guide light from a proximal end of said video-scope to the distal end of said video-scope;

a video-processor, to which said proximal end of said video-scope and a monitor for displaying said object image are respectively connected, adapted to process image-pixel signals corresponding to said object image, successively read from said image sensor;

a light source provided in said video-processor such that light, emitted from said light source, is guided through said light guide and radiates from the distal end of said video-scope;

a luminance value calculator adapted to successively calculate a luminance value indicating brightness of said object image on the basis of said image-pixel signals;

a stop provided between said light source and said proximal end of said video-scope, adapted to regulate a quantity of light radiating from the distal end of said video-scope;

a motor adapted to drive said stop, said stop being connected to said motor such that said stop is driven in accordance with a motion of said motor;

a drive-amount setter adapted to set a target drive-amount of said stop, to make brightness of said object image constant, on the basis of said luminance value;

a stop-controller adapted to adjust the quantity of light radiating from the distal end of said video-scope by controlling said stop in accordance with said target drive-amount at regular time-intervals, wherein said stop opens and closes such that the brightness of said object image displayed on said monitor is maintained at constant level; and a drive-amount determiner adapted to determine whether said target drive-amount exceeds a tolerable drive-amount, said stop-controller adapted to at least suspend a drive of said stop at the next adjustment of the quantity of light when said target drive-amount exceeds said tolerable drive-amount;

wherein when a drive-time of said stop, depending on the target drive-amount, exceeds the time-interval for performing the adjustment of the quantity of light, said stop-controller suspends the drive of said stop for at least the next adjustment of the quantity of light and substantially prevents hunting.

2. The electronic endoscope of claim 1, wherein said tolerable drive-amount is under a maximum drive-amount of a series of drive-amounts, said tolerable drive amount substantially preventing hunting.

3. The electronic endoscope of claim 1, wherein said motor is a stepping motor adapted to rotate in accordance with a pulse number of pulse signals, said stop-controller adapted to one of open and close said stop by rotating said stepping motor by a target pulse number corresponding to said target drive-amount, whereby said stop is adapted to be driven by said target pulse number.

4. The electronic endoscope of claim 3, wherein said stop-controller is adapted to adjust the quantity of light radiating from the distal end of said video-scope on the basis of a difference between said luminance value and a reference value indicating a proper brightness of said object image at regular-time-intervals.

5. The electronic endoscope of claim 4, wherein said drive-amount setter is adapted to set a target pulse number corresponding to said target drive-amount, on the basis of a reference table, in which a correspondence relationship between the difference of said luminance value and said reference value, and said target pulse number is indicated, said stop-controller adapted to one of open and close said stop by rotating said stepping motor by said target pulse number.

6. The electronic endoscope of claim 4, wherein said reference value is a middle value of a range of luminance values.

7. The electronic endoscope of claim 3, wherein said stop comprises:

a cover member adapted to cover light radiating from said light source toward said proximal end of said video-scope; and a support arm extended from said cover member, which is rotatably connected to said stepping motor, said stop adapted to pivot on said support arm such that the quantity of light radiating from the distal end of said video-scope is changed in accordance with a position of said cover member.

8. The electronic endoscope of claim 7, wherein said stop is pivotable between from an angle of approximately 0 degrees where said cover member covers all of light radiating from said light source and an angle of approximately 30 degrees where all of light radiating from said light source passes through said stop.

9. The electronic endoscope of claim 8, wherein said drive-amount determiner is adapted to determine whether said target pulse number exceeds a tolerable pulse number corresponding to a shifting-angle of 4 degrees of said stop.

10. The electronic endoscope of claim 1, wherein said luminance value is an average luminance value, which is an average value of one frame worth of luminance values.

11. The electronic endoscope of claim 1, further comprising a histogram-data generator adapted to successively generate a histogram-data on the basis of said image-pixel signals, said luminance value calculator adapted to read said histogram-data and then calculate an average luminance value, which is an average value of one frame worth of luminance values, on the basis of said histogram-data.

12. The electronic endoscope of claim 1, further comprising a single said stop.

13. The electronic endoscope of claim 1, wherein the luminance value is renewed every time said stop-controller adjusts the quantity of light.

14. The electronic endoscope of claim 1, wherein the regular time intervals correspond to a scanning time.

15. The electronic endoscope of claim 1, wherein when the drive-time of said stop, depending on the target drive-amount, exceeds the regular time-intervals for the adjustment of the light amount, said stop controller does not set the target drive amount and does not feed a drive signal to said stop for at least the next adjustment of the quantity of light.

16. A video-processor of an electronic endoscope, to which a proximal end of a video-scope and a monitor for displaying an object image are respectively connected, said video-scope having an image sensor provided at a distal end of said video-scope, on which an object image is formed, and a light guide provided throughout said video-scope, to guide light from the proximal end of said video-scope to the distal end of said video-scope, said video-processor processing image-pixel signals corresponding to said object image, read from said image sensor successively, so as to generate video signals and feed said video-signals to said monitor, said video processor comprising:

a light source provided in said video-processor such that light, emitted from said light source, is guided through said light guide and radiates from the distal end of said video-scope;

a luminance value calculator adapted to successively calculate a luminance value indicating brightness of said object image on the basis of said image-pixel signals;

a stop provided between said light source and the proximal end of said video-scope, adapted to regulate a quantity of light radiating from the distal end of said video-scope;

a motor adapted to drive said stop, said stop being connected to said motor such that said stop is driven in accordance with a motion of said motor;

a drive-amount setter adapted to set a target drive-amount of said stop, to make brightness of said object image constant, on the basis of said luminance value;

a stop-controller adapted to adjust the quantity of light radiating from the distal end of said video-scope by controlling said stop in accordance with said target drive-amount at regular time-intervals, wherein said stop opens and closes such that the brightness of said object image displayed on said monitor is maintained at constant level; and a drive-amount determiner adapted to determine whether said target drive-amount exceeds a tolerable drive-amount, said stop-controller adapted to at least suspend a drive of said stop at the next adjustment of the quantity of light when said target drive-amount exceeds said tolerable drive-amount;

wherein when a drive-time of said stop, depending on the target drive-amount, exceeds the time-interval for performing the adjustment of the quantity of light, said stop-controller suspends the drive of said stop for at least the next adjustment of the quantity of light and substantially prevents hunting.

* * * * *